US00PP12856P2

(12) United States Plant Patent
Zaiger et al.

(10) Patent No.: US PP12,856 P2
(45) Date of Patent: Aug. 13, 2002

(54) PLUM TREE NAMED 'CRIMSON GLO'

(76) Inventors: Chris Floyd Zaiger, 929 Grimes Ave.; Gary Neil Zaiger, 1907 Elm Ave.; Leith Marie Gardner, 1207 Grimes Ave.; Grant Gene Zaiger, 4005 California Ave., all of Modesto, CA (US) 95358

( * ) Notice: Subject to any disclaimer, the term of this patent is extended or adjusted under 35 U.S.C. 154(b) by 10 days.

(21) Appl. No.: 09/844,869

(22) Filed: Apr. 30, 2001

(51) Int. Cl.[7] ..... A01H 5/00
(52) U.S. Cl. ..... Plt./184
(58) Field of Search ..... Plt./184

*Primary Examiner*—Bruce R. Campell
*Assistant Examiner*—Anne Marie Grünberg

(57) ABSTRACT

A new and distinct variety of plum tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Heavy and regular fruit production.
2. Production of medium to large fruit with good flavor and eating quality.
3. Fruit with good storage and shipping quality.
4. Vigorous and upright growth.
5. Fruit with an attractive red flesh color.

1 Drawing Sheet

BACKGROUND OF THE VARIETY

In the field of plant genetics, we conduct an extensive and continuing plant-breeding program including the organization and asexual reproduction of orchard trees, and of which plums, peaches, nectarines, apricots, cherries and interspecifics are exemplary. It was against this background of our activities that the present variety of plum tree was originated and asexually reproduced by us in our experimental orchard located near Modesto, Stanislaus County, Calif.

PRIOR VARIETIES

Among the existing varieties of plums which are known to us, and mentioned herein, are 'Laroda' Plum (non-patented), 'Queen Ann' Plum (non-patented) and 'Friar' Plum (non-patented).

ORIGIN OF THE VARIETY

The new and distinct plum tree, (*Prunus salicina*), was developed by us in our experimental orchard as a first generation cross of a seedling with field identification number 46G731 with 'Friar' Plum (non-patented). The seedling 46G731 originated from a first generation cross of 'Laroda' Plum (non-patented) with 'Queen Ann' Plum (non-patented). A large group of these first generation seedlings were planted on their own root system, grow and maintained under close observation by us. One seedling, which is the present variety, exhibited distinct and desirable fruit characteristics, and was selected in 1989 for asexual propagation and commercialization.

ASEXUAL REPRODUCTION OF THE VARIETY

Asexual reproduction of the present variety of plum tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new and distinct variety of plum tree (*Prunus salicina*) is of large size, vigorous, upright growth and is a regular and productive bearer of medium to large, red flesh, clingstone fruit with good flavor and eating quality. The new fruit is nearly round in shape, has firm flesh with good storage and shipping quality, has resistance to cracking during rainy periods, holds firm on the tree 7 to 10 days after maturity (shipping ripe), and in comparison to 'Friar' Plum (non-patented) its pollen parent, the new variety has red flesh compared to yellow, is more round in shape, the skin is brownish violet in color compared to bluish black and is approximately 2 weeks earlier in maturity. In comparison to the 'Laroda' Plum (non-patented), the present variety is larger in size, has red flesh compared to amber yellow and is approximately 4 days earlier in maturity. In comparison to 'Queen Ann' Plum (non-patented), the present variety is nearly round in shape, compared to heart shape; the skin is brownish violet compared to yellowish mahogany and is approximately 7 days earlier in maturity.

PHOTOGRAPH OF THE VARIETY

The accompanying color photographic illustration shows typical specimens of the foliage and fruit of the present new plum variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of plum tree, its flowers, foliage and fruit, as based on observations of 10 year old specimens grown on 'Nemaguard' Rootstock (non-patented) near Modesto, Calif., with color terminology (except those in common terms) in accordance with Reinhold Color Atlas by A. Kornerup and J. H. Wanscher.

Tree:

*Size.*—Large. Normal for plum variety, pruned to 10 to 12 feet in height and width for economical harvesting of fruit.

*Vigor.*—Vigorous. Growth of 5 to 6 feet in height and 4 to 5 feet in width the first growing season, varies with soil condition, climate and cultural practices.

*Growth.*—Upright, usually pruned to vase shape. Heavy production of fruit has tendency to increase crotch angle and width of tree.

*Branching habit.*—Upright, production begins in third year and weight of fruit increases width of tree.

*Productivity.*—Productive, fruit set usually 2 or more times desired fruit, thinning and spacing of fruit necessary for desired fruit size.

*Bearer.*—Regular. Adequate fruit set for 8 consecutive years. No alternate fruit bearing observed.

*Fertility.*—Self-sterile, pollenizer required.

*Density.*—Medium dense. Usually pruned to vase shape to provide more uniform sunlight throughout the tree to enhance fruit color, increase Brix and improve growth of fruit bearing wood in center of tree.

*Hardiness.*—Tree grown in USDA Hardiness Zone 9. Chilling requirement approximately 750 hours at or below 45° F. Hardy in regard to all fruit growing areas of California.

Trunk:

*Size.*—Large. Average circumference of 20 inches at 10 inches above ground on 10 year old tree.

*Surface texture.*—Medium shaggy, as tree grows older, small areas of bark project outward, giving a rough or shaggy surface. Normal for plum trees, becomes rougher with age of tree.

*Color.*—Grayish brown to soot brown (6-E-3) to (6-F-5).

Branches:

*Size.*—Medium, normal for typical plum tree. Average circumference of 10 inches at 33 inches above ground. Crotch angle approximately 30°, increases with heavy crop load.

*Surface texture.*—Smooth on new growth to medium rough on mature growth.

*Lenticels.*—Color — yellowish orange to grayish orange (5-A-5) to (5-B-5). Average number 29 in 4 square inch surface. Average length — 3/32 inch. Average width — 1/32 inch.

*Color.*—New growth varies from greenish olive brown to brownish yellow (4-F-7) to (5-C-8); older, mature branches vary from oak brown to linoleum brown (5-D-6) to (5-E-7).

Leaves:

*Size.*—Medium. Average length — 3½ inches. Average width — 1⅜ inches.

*Form.*—Oblanceolate, apex acuminate, base cuneate.

*Margin.*—Doubly serrate.

*Thickness.*—Medium, normal for most plum leaves.

*Surface.*—Upper surface relatively smooth, slightly indented over leaf veins, glabrous. Lower surface relatively smooth, small ridges created by midrib and pinnate venation, glabrous.

*Petiole.*—Average length — 5/8 inch. Average width — 1/16 inch. Color — grayish green to bile yellow (30-B-5) to (30-C-5)

*Glands.*—Globose. Size — very small, rounded. Average diameter 1/32 inch. Number varies from 0–4, average number 2. Located on upper portion of petiole and lower portion of leaf blade. Color — reddish blond (5-C-4), becomes darker with age of leaf.

*Color.*—Upper surface green to dark green (29-F-5) to (29-F-7). Lower surface light green to spinach green (28-E-5) to (28-E-6).

Flower buds:

*Size.*—Small. Average length 5/16 inch. Average diameter ¼ inch. Three days before bloom.

*Hardiness.*—Grown in USDA Hardiness Zone 9. Hardy in all stone fruit growing areas of California.

*Form.*—Plump, conical. Becomes elongated before opening.

*Pedicel.*—Average length — ½ inch. Average width — 3/64 inch. Color light green to yellowish green (2-B-3) to (2-B-5).

*Color.*—White (1-A-1).

*Number of buds per spur.*—Average number 4. Varies from 2 to 9, primarily with age of spur.

Flowers:

*Size.*—Medium. Average height ½ inch. Average diameter 29/32 inch.

*Petal.*—Number — 5, alternately arranged to sepals. Shape — ovate. Size — medium. Average length 15/32 inch. Average diameter 5/16 inch, smaller at point of attachment. Color — white (1A-1). Outer edge of petal varies from smooth to scalloped.

*Sepals.*—Size — medium. Number — 5, alternately arranged to petals. Color — lower surface, medium green (29-D-8). Upper surface yellowish green (29-C-8). Surface — upper and lower glabrous.

*Stamens.*—Number varies from 30 to 44 per flower. Average number 37. Average length 19/64 inch. Filament color white (1-A-1). Anther color light orange (5-A-5).

*Pollen.*—Present, self-sterile, pollenizer required. Color — pale yellow to yellow (4-A-3) to (4-A-5).

*Pistil.*—Number — normally 1, varies from 1 to 2. Average length 13/32 inch. Color — pastel yellow to light yellow (1-A-4) to (1-A-5). Stigma approximately 3/64 inch above anthers.

*Fragrance.*—Very slight.

*Blooming period.*—Date of First Bloom Feb. 22, 2000. Date of Petal Fall Mar. 6, 2000. Varies slightly with climatic conditions.

*Color.*—White (1-A-1).

*Number of flowers per bud.*—Normally 2, Varies from 1 to 3.

*Pedicel.*—Average length 33/64 inch. Average width 1/16 inch. Color — yellowish green (30-B-8).

Fruit:

*Maturity when described.*—Firm ripe.

*Date of first picking.*—Jul. 4, 2000.

*Date of last picking.*—Jul. 10, 2000. Varies slightly with climatic conditions.

*Size.*—Average diameter axially — 2 to 2⅛ inches. Average transversely in suture plane 2⅜ inches to 2½ inches. Average weight 116.4 grams. Average weight varies slightly with fertility of the soil, amount of thinning and climatic conditions.

*Form*.—Nearly globose, slightly elongated.

*Suture*.—Shallow, extends from base to apex.

*Ventral surface*.—Nearly smooth, only slightly lipped.

*Apex*.—Slightly retuse.

*Base* .—Retuse.

*Cavity*.—Rounded, slightly elongated in suture plane. Average depth ¼ inch. Average breadth ½ inch.

Stem:

*Size*.—Average length ⅝ inch. Average diameter 1/16 inch.

*Color*.—Light green to yellowish green (30-D-6) to (30-D-8).

Flesh:

*Ripens*.—Evenly.

*Texture*.—Firm, meaty.

*Fibers*.—Few, small, tender.

*Firmness*.—Firm, comparable to the flesh of 'Friar' Plum (non-patented).

*Aroma*.—Slight.

*Amydgalin*.—Undetected.

*Eating quality*.—Good.

*Flavor*.—Good. Good balance between sugar and acid.

*Juice*.—Moderate, enhances flavor.

*Brix*.—15.8°. Varies slightly with amount of fruit per tree and climatic conditions.

*Color*.—Varies from pale red to deep red (10-A-3) to (10-C-7), darkest near surface of skin. Color increases with maturity of fruit. Pit cavity color varies from dark red to brownish red (10-C-8) to (10-D-8).

Skin:

*Thickness*.—Medium, shows minimal scarring or tearing during picking and packing trials.

*Texture*.—Smooth, without roughness or reticulation, similar to 'Friar' Plum (non-patented).

*Bloom*.—Moderate, complete coverage.

*Tendency to crack*.—None.

*Color*.—Yolk yellow to curry yellow (4-B-8) to (4-C-8) ground color. Overspread with brownish violet to violet brown (10-F-5) to (10-F-8). Small, randomly spaced areas of ground color showing, leaving a speckled pattern to skin.

*Tenacity*.—Tenacious to flesh.

*Astringency*.—None.

Stone:

*Type*.—Clingstone.

*Size*.—Medium. Average length 53/64 inch. Average width 21/32 inch. Average thickness 7/16 inch.

*Form*.—Obovoid.

*Base*.—Straight.

*Apex*.—Nearly rounded, very slight point. Average length 1/32 inch.

*Surface*.—Lightly pitted throughout, a shallow groove on each side of suture extending from base to apex, a small narrow ridge in the center on each side of stone running from base to apex. Several small, narrow ridges extending from base approximately one third of the distance toward apex.

*Sides*.—Equal to unequal. Some stones having one side extending further from suture plane.

*Tendency to split*.—None.

*Color*.—Light brown to yellowish brown (5-C-6) to (5-D-8) when dry.

Kernel:

*Average length*.—37/64 inch.

*Average width*.—25/64 inch.

*Seed coat color*.—Tan to grayish orange (5-B-4) to (5-B-5) when dry.

*Taste*.—Bitter.

*Amydgalin*.—Abundant.

Use: Dessert. Market, local and long distance.

Keeping quality: Good, held firm in cold storage for 2 weeks at 38 to 42° F. with no internal breakdown or appreciable loss of eating quality.

Shipping quality: Good, picking and packing of fruit gave minimal skin scarring or bruising of flesh.

Disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of plum tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of plum tree, substantially as illustrated and described, characterized by its large size, vigorous, upright growth and being a productive and regular bearer of medium to large, clingstone fruit with good flavor and eating quality; the fruit is further characterized by having firm red flesh, good storage and shipping quality and in comparison to the 'Friar' Plum (non-patented), which has fruit with yellow flesh and bluish black skin color, the new variety has red flesh, brownish violet skin color and the fruit is two weeks earlier in maturity.

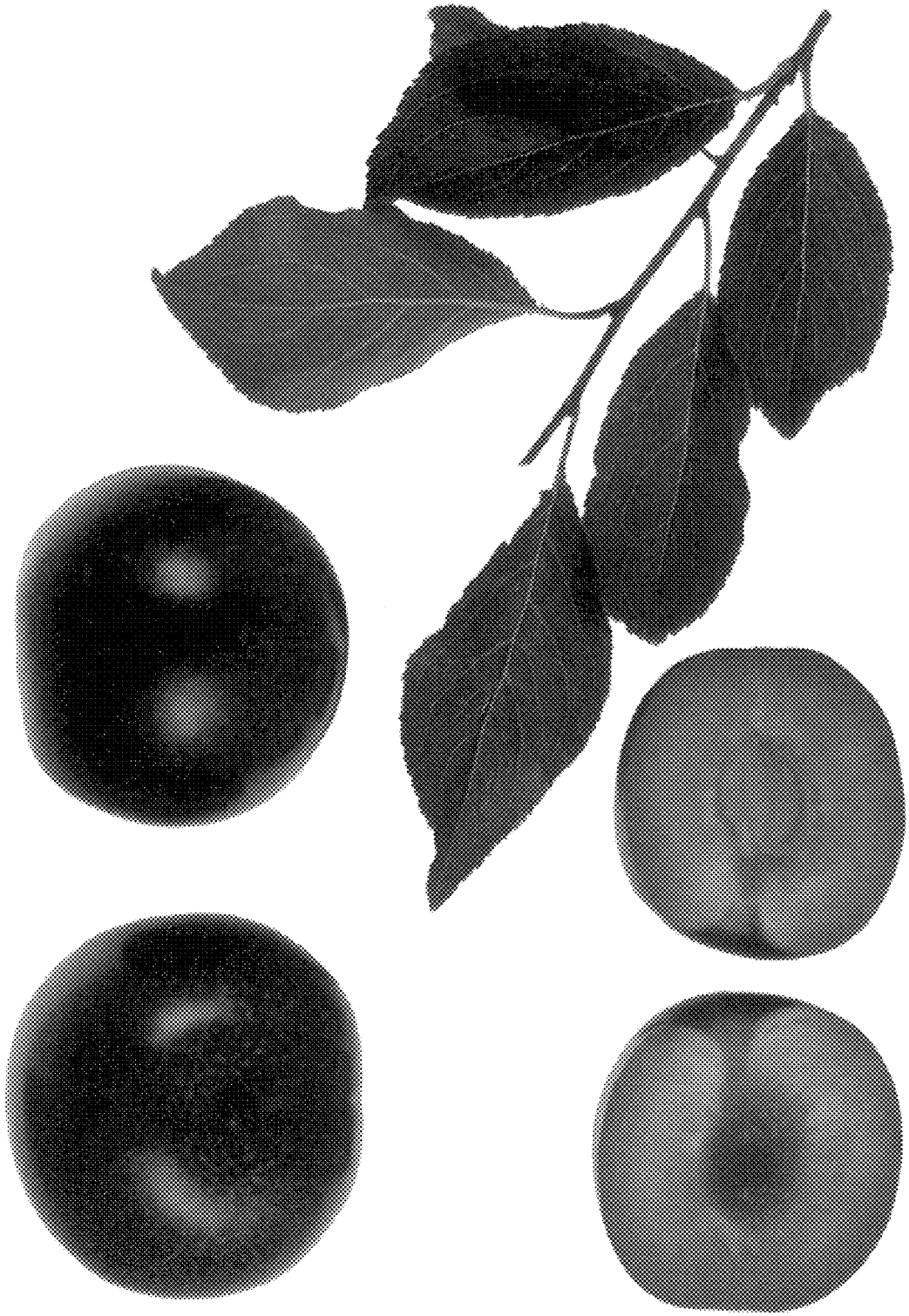

* * * * *